(12) United States Patent
Waer et al.

(10) Patent No.: US 7,253,176 B1
(45) Date of Patent: Aug. 7, 2007

(54) IMMUNOSUPPRESSIVE EFFECTS OF 8-SUBSTITUTED XANTHINE DERIVATIVES

(75) Inventors: Mark Jozef Albert Waer, Heverlee (BE); Piet André M. M. Herdewijn, Rotzelaar/Wezemaal (BE); Wolfgang Eugen Pfleiderer, Constance (DE)

(73) Assignee: K.U. Leuven Research & Development (BE)

( * ) Notice: Subject to any disclaimer, the term of this patent is extended or adjusted under 35 U.S.C. 154(b) by 0 days.

(21) Appl. No.: 09/564,200

(22) Filed: May 4, 2000

(51) Int. Cl.
*A61K 31/519* (2006.01)

(52) U.S. Cl. .............................. 514/263.2; 514/264.1; 514/265.1

(58) Field of Classification Search ........ 514/263–265, 514/263.2, 264.1, 265.1
See application file for complete search history.

(56) References Cited

U.S. PATENT DOCUMENTS 4,879,296 A * 11/1989 Daluge et al. ............ 514/263.2
5,559,121 A * 9/1996 Harrison et al. ............ 514/291

FOREIGN PATENT DOCUMENTS

| EP | 0490181 | | 6/1992 |
|---|---|---|---|
| WO | WO 95/11681 | * | 5/1995 |
| WO | 9636638 | | 11/1996 |

OTHER PUBLICATIONS

Katzung, B.G., Basic and Clinical Pharmocology, 6th ed., 1995, p. 864-865.*
Functionalized Congeners of 1,3-Dialkylxanthines: Preparation of Analogues with High Affinity for Adenosine Receptors; Jacobson et al.; 1985; vol. 28, pp. 1334-1340.
8-Substituted Xanthines as Antagonists at $A_1$- and $A_2$- Adenosine Receptors; Jacobson et al.; 1988; vol. 37, pp. 3653-3661.
Sulfur-Containing 1,3-Dialkylxanthine Derivatives as Selective Antagonists at $A_1$-Adenosine Receptors; Jacobson et al.; 1989; vol. 32, pp. 1873-1879.
Effect of Trifluoromethyl and Other Substituents on Activity of Xanthines at Adenosine Receptors; Jacobson et al.; 1993; vol. 36, pp. 2639-2644.
Effects of 8-Phenyl and 8-Cycloalkyl Substituents on the Activity of Mono-, Di-, and Trisubstituted Alkylxanthines with Substitution at the 1-, 3-, and 7-Positions; Shamim et al.; 1989; vol. 32, pp. 1231-1237.
Synthesis of Paraxanthine Analogs (1,7-Disubstituted Xanthines) and Other Xanthines Unsubstituted at the 3-Position: Structure-Activity Relationships at Adenosine Receptors; Müller et al.; 1993; vol. 36, pp. 3341-3349.
QSAR studies of 8-substituted xanthines as adenosine receptor antagonists; Doichinova et al.; 1994; vol. 29, pp. 133-138.
Use of Methylxanthine Derivative A802715 in Transplantation Immunology; Lin et al.; 1997; vol. 63, pp. 1734-1738.
$A_1$ Adenosine Receptor Antagonists as Ligands for Positron Emission Tomography (PET) and Single-Photon Emission Tomography (SPET); Holschbach et al.; 1998; vol. 41, pp. 555-563.
M. Mayne et al., Dysregulation of Adenosine $A_1$ Receptor-Mediated Cytokine Expression in Peripheral Blood Mononuclear Cells from Multiple Sclerosis Patients, *Ann. Neurol.*, 1999, pp. 633-639, vol. 45.
G. Hasko et al., Adeonsine: a potential mediator of immunosuppression in multiple organ failure, *Current Opinion in Pharmacology*, 2002, pp. 440-444, vol. 2, Elsevier Science Ltd.

* cited by examiner

*Primary Examiner*—San-Ming Hui
(74) *Attorney, Agent, or Firm*—The Webb Law Firm

(57) ABSTRACT

The invention relates to a novel use of 8-substituted xanthine derivatives for the manufacture of a medicament for the treatment of auto-immuno disorders.

4 Claims, No Drawings

IMMUNOSUPPRESSIVE EFFECTS OF 8-SUBSTITUTED XANTHINE DERIVATIVES

The invention relates to a novel use of 8 substituted xanthine derivatives for the manufacture of a medicament for the treatment of auto-immuno disorders.

Methylxanthines, for example pentoxifylline (PTX) are known having immunosuppressive effects in vitro.

Several types of 8-substituted xanthine derivatives have been publicized, for example K. A. Jacobson et al. J. Med. Chem. 1993, 36, 2639–2644; K. A. Jacobson et al. Biochem. Pharmacol. 1988, 37, 3653–3661; K. A. Jacobson et al. J. Med. Chem. 1989, 32, 1873–1879.

Recently (Lin Y. et al, Transplantation 63 (1997) it has been found that the co-medication of an immunosuppressive compound such as cyclosporine A (CyA) or FK506 or RPM (rapamycine) with a methyl xanthine derivative, in particular A802715 (7-propyl-1(5-hydroxy-5-methylhexyl)-3-methylxanthine) leads to a superadditive increase in the immunosuppressive action.

The immunosuppressive effect of cyclosporine A (CyA) is already known since 1972. However, due to its nephrotoxicity and several other side effects CyA has not been able to establish itself as the optimal and final drug of choice.

The present invention relates to a novel use of 8-substituted xanthine derivates and their pharmaceutical salts, possessing unexpectedly desirable pharmaceutical properties, i.c. are immunosuppressive agents.

The invention demonstrates a novel use of xanthine derivatives of the formula (I):

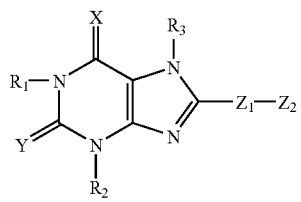

wherein:

$R_1$, $R_2$ and $R_3$ are independently hydrogen, saturated or unsaturated aliphatic chains which may be straight or branched having 1 to 6 carbon atoms;

X and Y are independently oxygen or sulfur;

$Z_1$ is selected from the group comprising a thienyl; furanyl; cyclopentyl or a substituted by $Z_2$ or unsubstituted phenyl; wherein $Z_2$ is selected from the group comprising phenyl; sulfonic acid; unsubstituted or N-substituted sulfonamide with substituents such as alkyl, aminoalkyl where the amino group may be substituted itself with lower alkyl groups bearing 1 to 4 carbon atoms; nitro; substituted or unsubstituted amino group; aliphatic chain with 1 to 3 carbon atoms; halogenated aliphatic chain with 1 to 3 carbon atoms; aliphatic chain containing ether functions, acids, esters, amides, substituted or unsubstituted amines having 1 to 3 carbon atoms, nitro, sulfonamides or a combination of these functional groups with a maximum length of the chain of 12 atoms, or a pharmaceutically acceptable salt thereof for the manufacture of a medicament for the treatment of auto-immuno disorders.

The invention further relates to a combination preparation, containing 1) cyclosporin A or FK506 or rapamycin, 2) at least one 8-substituted xanthine derivative of formula (I), and optionally a pharmaceutical excipient, for simultaneous, separate or sequential use in (auto)immune disorders.

Hereunder the effects of the 8-substituted xanthine derivatives on the lymphocyte activation are elucidated and are compared with non-substituted xanthine derivatives (see table I, compound 1, 2, 3, 4, 5, 22, 23, 24, 25, 26, and 67, 68, 69, 70, 71).

Table I summarizes the tested compounds. These xanthine derivatives were obtained as follows:

Compound number 8, 10, 12, 14, 21, 36, 37, 38, 47, 48, 50, 51, 79, 83

K. A. Jacobson et al. J. Med. Chem. 1993, 36, 2639–2644;

9, 11, 13, 30, 31, 39, 40, 41, 42, 43, 125

K. A. Jacobson et al. Biochem. Pharmacol. 1988, 37, 3653–3661;

15, 17, 18, 28, 29, 33, 34, 35, 44, 45, 46, 55, 56, 57, 58, 59, 60, 61, 62, 63, 64, 65, 78, 80, 81

K. A. Jacobson et al. J. Med. Chem. 1989, 32, 1873–1879;

Compound numbers 1, 2, 3, 4, 5, 22, 23, 24, 67, 68, 82, 112, 113, 114, 116, 117, 118, 119 (table I and II) were obtained by the following procedure for the alkylation of xanthine derivatives.

0,01 mol of a xanthine derivative (1a, 2a, 3a, 4a, 5a, 67a, 68a, 82a, 112a, 113a (114a), 116a (117a), 118a (119a)). [The origin of these compounds is as follows: 1a Theobromin, commercially available FLUKA AG; 2a W. Traube, Ber. Deut. Chem. Ges. 33, 3035 (1900); 3a G. Elion, J. org. Chem. 27, 2478 (1962); 4a W. Hutzenlaub, W. Pfleiderer, Liebigs Ann. Chem. 1979, 1847; 5a Xanthin, commercially available FLUKA AG; 67a W. Hutzenlaub, W. Pfleiderer, Liebigs Ann. Chem. 1979, 1847; 68a P. G. Kjellin, C. G. A. Persson, Eur. Pat. Appl. 10 531; C.A. 94, P 15773 u; 82a K. A. Jacobson, D. Shi, C. Gallo-Rodriguez, M. Manning, C. Müller, J. W. Daly, J. L. Neumeyer, L. Kiriasis, W. Pleiderer, J. Med. Chem. 36, 2639 (1993); 112a R. Goldner, G. Dietz, E. Carstens, Liebigs Ann. Chem. 691, 142 (1966); 113a M. T. Shamim, D. Ukena, W. L. Padgett, J. W. Daly, J. Med. Chem. 32, 1231 (1989)] (see table II) were suspended or dissolved in DMF (60 ml) at room temperature and then under stirring $K_2CO_3$ (6 g per N—H function) and the alkylating agent (methyl iodide, ally iodide, propargyl bromide, n-propyl iodide, benzyl bromide, 2-chlorobenzyl bromide, 4-bromo-butanoic acid, 5-bromopentanoic acid, ethyl 4-bromobutanoate) (0.015 mol per N—H) function added. The mixture was stirred at room temperature for 15 h, then the insoluble inorganic salts filtered off by suction and the filtrate evaporated in vacuum at 50° C. to a syrup. The residue was treated with $H_2O$ forming a colorless solid. The precipitate was collected and purified by recrystallization from $H_2O$/EtOH mixtures to give colorless crystals of 1, 2, 3, 4, 5, 67, 68, 82, 112, 113, 114, 116, 117, 118, 119.

Compound numbers 16, 52, 53, 54, 69, 70, 71, 115, 116a (117a), 118a (119a) (table I and III) were obtained by a procedure for the cyclization of 5-acylamino-6-aminouracils

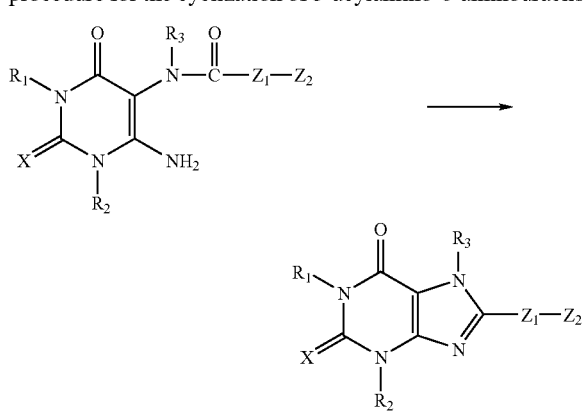

The 5-acylamino-6-aminouracil (16a, 52a, 53a, 54a, 69a, 70a, 71a, 115a, 136b, 118b) (0.01 mol) was heated in a mixture of 2 NaOH (50 ml) and EtOH (10 ml) under reflux for 30 min. The hot solution was acidified by ACOH whereby a colorless precipitate separated. The solid was collected after cooling, dried and then purified by recrystallization from EtOH, DMF or by reprecipitation from alkaline solution by addition of AcOH.

General Procedures for the Synthesis of 5-acylamino-6-aminouracils (16a, 52a, 53a, 54a. 69a, 70a, 71a, 115a, 116b, 118b) (Table IV).

a) 0.01 mol of the N-substituted 5,6-diaminouracil (69b, 70b, 71b) was heated in formic acid (20 ml) for 15 min under reflux. The reaction mixture was evaporated to dryness and the residue recrystallized from water to give colorless crystals (69a, 70a, 71a). Yield: 75–90%.

b) 0.01 mol of the N-substituted 5,6-diaminouracil (52b, 53b, 116c) was treated with 0.012 mol of the appropriate acyl chloride (p-nitrobenzoyl chloride, p-biphenyl-4-carbonyl chloride, p-chlorbenzoyl chloride, p-aminobenzoyl chloride) in abs. pyridine (20 ml) with stirring at room temp. for 3 hours. It was evaporated, the residue treated with water and the resulting precipitate collected by suction. Recrystallization from EtOH/H$_2$O yielded 70–90% of colorless crystals (52a, 15a, 53a, 54a, 116b, 118b).

c) 0.01 mol of the N-substituted 5,6-diaminouracil (16b) was suspended in EtOH (100 ml), then subsequently added 0.011 mol of the appropriate acid (p-sulfamoylbenzoic acid) and 0.012 mol of the condensing agent (dicyclohexylcarbodiimide), N-dimethylaminopropyl-N'-ethylcarbodiimide hydrochloride). The mixture stirred at room temp. for 2 hours, the precipitate filtered off and purified by recrystallization from EtOH to give colorless crystals (16a). Yield: 80–90%.

General Procedure for the Synthesis of N-alkyl-5,6-diaminouracil (16b, 52b, 53b, 69b, 70b, 71b, 116c) (Table V).

a) 0.05 mol of 6-amino-3-methyl-1-neopentyluracil (69c), 6-amino-1,3-dimethyluracil (52c), 6-amino-1,3-di-n-propyluracil (53c), 6-amino-1-isopropyl-3-methyluracil (71c), 6-amino-1-n-propyluracil (116d) and 6-amino-1,3-di-n-propyl-2-thiouracil (16c), respectively, were suspended in a mixture of water (100 ml) and EtOH (20 ml) and heated to 50° C. Then NaNO$_2$ (4 g) was added and the stirring mixture acidified by dropwise addition of AcOH (5 ml) whereby intermediary solution with strong coloration takes place. A red to violet coloured precipitate consisting of the corresponding 5-nitroso derivative was formed. The solid was collected after cooling (85–90%) and used directly for reduction to the anticipated N-alkyl-5,6-diaminouracil (69b, 52b, 53b, 71b, 116c, 16b). 0.05 mol of the 6-amino-N-alkyl-5-nitrosouracil derivative was added under stirring to a warm solution (50° C.) of ammonium sulfide (25 ml) and then the temperature raised to 80° C. for 15 min. On cooling the resulting precipitate was filtered off by suction, washed with water and little MeOH and then dried in a vacuum desiccator to give 75–90% of colorless to yellowish crystals.

b) 6-Amino-5-methylamino-1-neopentyluracil (70b). 6-Amino-1-neopentyluracil (70c) (3.94 g, 0.02 mol) was treated in AcOH (40 ml) at 80° C. in presence of NaOAc×3H$_2$O (2.6 g, 0.02 mol) with bromine (3.2 g, 0.02 mol) by dropwise addition. After 2 hours was cooled, the precipitate (75%) collected, washed with water and dried. 6-Amino-5-bromo-1-neopentyluracil (2.76 g, 0.01 mol) was then stirred in a 40% aqueous methylamine solution (80 ml) at room temp. for 2 days. The mixture was evaporated to half its volume and the precipitate collected. Washing with water and drying in a desiccator yielded 2.05 g (90%) of 70b. M.P. 217–220° C.

Syntheses of N-alkyl-6-aminouracils.

6-Amino-1-neopentyluracil (70c). N-neopentylurea (13.0 g, 0.1 mol) and ethyl cyanoacetate (10 ml) were heated in 4N NaOEt (100 ml) for 4 hours under reflux. The reaction mixture was evaporated to dryness, the residue treated with water (100 ml) and then acidified with AcOH to pH 4–5 to form a colorless precipitate. Yield: 11.2 g (59%).

6-Amino-3-methyl-1-neopentyluracil (69c). 6-Amino-1-neopentyluracil (90c) (5.9 g, 0.03 mol) were dissolved in 1 N NaOH (50 ml) and then under vigorous stirring dimethylsulfate (3.9 ml, 0.033 mol) dropwise added at room temp. A precipitate separated and was collected after 2 hours. After washing with water and drying in a vacuum desiccator resulted 5.76 g (91%) of colorless crystals.

6-Amino-3-methyl-1-n-isopropyluracil (71c). 6-Amino-1-isopropyluracil (16.9 g, 0.1 mol) were dissolved in 1 N NaOH (120 ml) and then at room temp. dimethylsulfate (12 ml, 0.12 mol) dropwise added with vigorous stirring. After 1 hour the precipitate was collected, washed with water and dried at 50° C. in high vacuum to give 15.1 g (82%) of chromatographically pure, colorless crystals.

6-Amino-1-n-propyluracil (116d). N-n-propylurea (20.4 g, 0.2 mol) and ethyl cyanoacetate (20 ml) were heated in 3 N NaOMe (200 ml) for 3 hours under reflux. The reaction mixture was evaporated, the residue treated with 100 ml of water and acidified with AcOH to pH 4 to give 23.7 g (70%) of colorless crystals.

6-Amino-1,3-di-n-propyl-2-thiouracil (16c). To a mixture of cyanoacetic acid (10 g) and acetic anhydride (50 ml) was added N,N'-di-n-propylthiourea (16 g, 0.01 mol) and stirred at 60° C. for 4 hours. It was evaporated to dryness, the residue treated with 30% NaOH (100 ml) for 30 min, then diluted with water (100 ml) and the precipitate collected. Recrystallization from EtOH/water gave 18 g (79%) of yellowish crystals. The same procedure and started from N,N'-dimethylurea or N,N'-di-n-propylurea yielded 6-amino-1,3-dimethyluracil (52c) and 6-amino-1,3-di-n-propyluracil (53c) respectively as colorless crystals.

Compound numbers 25 and 26 (table I and table III) were obtained by a general procedure for the synthesis of 1-(5-hydroxyhexyl)xanthines.

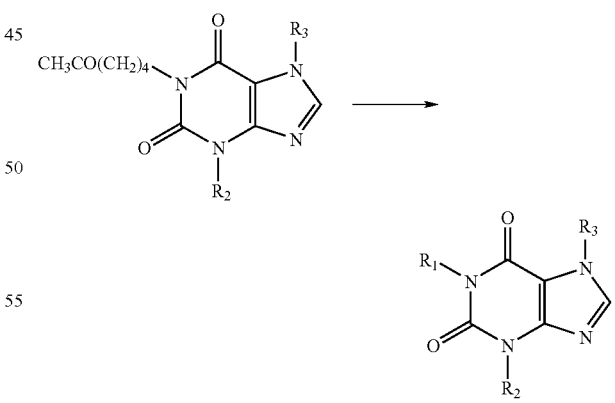

3,7-Dialkyl-1-(hexan-5-onyl)xanthine (2 mmol) was dissolved in MeOH (15 ml) and then treated under stirring with NaBH$_4$ (0.1 g) overnight. The mixture was evaporated to dryness, the residue diluted with H$_2$O, then extracted several times with CHCl$_3$. The CHCl$_3$ layer was dried over Na$_2$SO$_4$, filtered and the filtrate again evaporated to give a chromatographically pure solid. The solid was stirred in n-hexane for 1 h, then filtered by suction and dried in a vacuum destillator to give a colorless crystal powder.

Compounds 19, 20 and 66 were obtained by methylation of 55, 57 and 64 respectively. 0.01 Mol of the purine 55, 57 and 64, respectively, was dissolved in DMF (120 ml) by warming. After cooling to room temperature $K_2CO_3$ (7 g) and methyl iodide (2 ml) were added and then the mixture stirred for 3 hours. The solution was then diluted with $H_2O$ (150 ml) and after cooling the precipitate collected, washed with water and dried. Recrystallization from $EtOH/H_2O$ gave colorless crystals in 75–90% yield. M.p. 198° C. (19), 298° C. (20) and 197° C. (66).

The synthesis of compound 32 is based on compound 33, which is described in literature [K. A. Jacobson, K. L. Kirk, W. L. Padgett, J. W. Daly, J. Med. Chem. 1985, 28, 1334]. Compound 33 (2.14 g, 0.005 mol) was suspended in abs. pyridine (50 ml) and then under stirring chlorosulfonic acid (4 ml) added dropwise. It was heated to 50° C. with stirring for 12 hours. The reaction mixture was evaporated in vacuum, coevaporated twice with EtOH and the residue recrystallized from $H_2O/EtOH$ to give 1.95 g (77%) of 32 of a colorless crystal powder. M.p. 245° C.

Materials and Methods

Various models may be used for testing an immunosuppressive effect. In vivo, for example, different transplantation models are available. They are strongly influenced by different immunogenicities, depending on the donor and recipient species used and depending on the nature of the transplanted organ. The survival time of transplanted organs can thus be used to measure the suppression of the immune response. In vitro, there exist also various models. The most used are lymphocyte activation tests. Usually activation is measured via lymphocyte proliferation. Inhibition of proliferation thus always means immunosuppression under the experimental conditions applied. There exist different stimuli for lymphocyte activation:

- coculture of lymphocytes of different species (MLR=mixed lymphocyte reaction): lymphocytes expressing different minor and major antigens of the HLA-DR type (=allogens) activate each other non-specifically.
- CD3 assay: here there is an activation of the T-lymphocytes via an exogenously added antibody (OKT3). This antibody reacts against the CD3 molecule located on the lymphocyte membrane. This molecule has a costimulatory function. The interaction anti-CD3 (=OXT3)-CD3 results in T-cell activation which proceeds via the $Ca^{2+}$/calmodulin/cacineurin system and can be inhibited by CyA.
- CD28 assay: here specific activation of the T-lymphocyte goes also via an exogenously added antibody against the CD28 molecule. This molecule is also located on the lymphocyte membrane, and delivers strong costimulatory signals. This activation is $Ca^{2+}$-independent and thus cannot be inhibited by CyA.
- IL-2R assay: here activation of the lymphocyte occurs via the exogenously added cytokine IL-2 which binds to the IL-2 receptor (IL-2R) that is located on the lymphocyte membrane of prestimulated T cells. This activation is also $Ca^{2+}$/cAMP-independent and cannot be inhibited by CyA.

Reagents

All derivatives were dissolved in 0.5 ml DMSO and further diluted in culture medium before use in in vitro experiments. The culture medium consisted of RPMI-1640+ 10% FCS.

Mixed Lymphocyte Reaction

Peripheral blood mononuclear cells (PBMC) were isolated from heparinized peripheral blood by density gradient centrifugation over Lymphoprep (Nycomed, Maorstua, Norway). Allogeneic PBMC or EBV-transformed human B cells [RPMI1788 (ATCC name CCL156)] which strongly express B7-1 and B7-2 were used as stimulator calls after irradiation with 30 Gy. MLR was performed in triplicate wells. After 5 days incubation at 37° C., 1 µCi [$^3$H]-thymidine was added to each cup. After a further 16 hours incubation, cells were harvested and counted in a β-counter.

The percent suppression of proliferation by drugs was counted using the formula:

$$\text{Percent inhibition} = \frac{(\text{cpm} + \text{drugs}) - \text{cpm } Cult.Med.)}{(\text{cpm} - \text{drugs}) - \text{cpm } Cult.Med.)} \times 100$$

T Cell Purification

T cells were purified by removing non-T cells. Briefly, monocytes were removed by cold agglutination. The resulting lymphoid cells were further purified by a cell enrichment immunocolumn [Cellect Human T (Biotex, Edmonton, Alberta, Canada)] by a process of negative selection. More than 95% of the B cells were removed with this procedure. After depletion, the resulting T cell preparation was highly purified explaining these cells could not be activated by PHA or rIL-2 alone at concentrations capable of stimulating RBMC prior to deletion.

Measurements of T Cell Proliferations Induced by Anti-CD3 mAB+PMA or Anti-CD28 mAb+PMA Highly purified T cells ($10^6$/ml) were stimulated by immobilized anti-CD3 or anti-CD28 mAb in the presence of PMA. Anti-CD3 mAb (CLB-CD3; CLB, Amsterdam, The Netherlands) were fixed on the 96-microwell plates by incubating the wells with 50 µl of mAb solution (CLB-CD28; CLB, Amsterdam, The Netherlands) 50 µl (1/650 dilution in culture medium) was added directly to the wells. Further, 20 µl PMA (Sigma, St. Louis, Mo., USA) solution (final concentration: 0.5 ng/ml) was added. Subsequently, 20 µl of immunosuppressants were added by serial dilution in triplicate wells. Finally 100 µl of the T cell suspension ($10^6$/ml) was added. After 48-hour incubation at 37° C. in 5% $CO_2$ 20 µl BrdU (100 µM solution) (Cell Proliferation Elisa, Boehringer-Mannheim Belgium) was added to each well. After a further overnight incubation the T cell proliferation was measured using a calorimetric immunoassay for qualification of cell proliferation based on measurements of the incorporation of BrdU during DNA synthesis. The optical density (OD) was measured by a Behring EL311 place reader at 450 nm (reference wavelength: 690 µm). The percent suppression of proliferation by drugs was counted using the formula:

$$\text{Percent inhibition} = \frac{(OD + \text{drugs}) - OD \ Cult. \ Med.)}{(OD - \text{drugs}) - OD \ Cult. \ Med.)} \times 100$$

In Vitro Immunosuppressive Effect of Xanthine Derivatives as Measured with the MLR and with Tests Involving Polyclonal T Cell Proliferation Induced by Anti-CD3 mAb+PMA or Anti-CD28 mAb+PMA (Table VI)

In the table VI column II shows the IC50 values of the various substances in the MLR. The IC50 value represents the lowest concentration of the substances that resulted in a 50% suppression of the MLR.

Column III shows the IC50 value of the various substances for the anti-CD3 mAb+PMA pathway and row IV the IC50 values of the various substances for the anti-CD28 mAb+PMA pathway.

As a comparison the values of other immunosuppressants: CsA, FK506, Rapamycin, Leflunomide and Mycophenolic acid are given as well.

Whole Blood Assay (WBA): WBA is a lymphoproliferation assay performed in vitro but using lymphocytes present in whole blood, taken from animals that were previously given test substances in vivo. Hence it reflects the in vivo effect of substances as assessed with an in vitro read-out assay.

Rats: inbred, male 6- to 8-weeks old R/A rats weighing ±200 g were used as recipients.

Drug administration: xanthine derivatives were dissolved in DMSO and further diluted with PBS. Products were given orally in different concentrations 2 times a day for 2 days. To perform the experiments, 6–8 hours after the last administration 1 ml of blood is taken by heart puncture after ether anesthesia and anticoagulated with 100 U/ml of preservative free heparine.

Whole Blood Assay: This assay was performed as we described previously (Use of the Methylxanthine Derivatives A802715 in Transplantation Immunology. II In vitro Experiments. (Yuan Lin, et al., Transplantation 1997, 63, No. 12, 1734–1738)].

Heparinized whole blood was diluted (1:25) with complete RPMI medium and stimulated with 15 µg/ml of concanavalin A (Con A) in triplicate wells in 96-well microtiter plates at 37° C. and 5% $CO_2$. After 96-h culture, proliferation was determined by measuring the incorporation (cpm) of [$^3$H]-thymidine.

The Con A induced proliferation of lymphocytes taken from rats receiving the test substances (exp) was compared with that from rats receiving only the solvent (con). The percent suppression was calculated as follows:

$$\% \text{ suppression: } 100 - \left[\frac{\text{cpm exp}}{\text{cpm con}} \times 100\right]$$

| | | Results | |
|---|---|---|---|
| Nr | % suppresion | Administration of drugs | Blood taken after: |
| 11 | 33 | 40 mg/kg/d 2x/d 2d | 8 h |
| 14 | 86 | 40 mg/kg/d 2x/d 2d | 8 h |

First, most of the substances according to the invention have a clear suppressive effect in the MLR (mixed lymphocyte reaction). The MLR is considered as an in vitro analogue of the transplant rejection as it is based on the recognition of allogeneic MHC (major histocompatibility antigens) on the stimulator leucotyes, by responding lymphocytes. Various established immunosuppressive drugs are known to suppress the MLR, and were also shown in this description. Further, the 8-substituted xanthine derivatives are more effective than the non-substituted.

From these data it can be deduced that the 8-substituted xanthine derivatives may be effective in clinical situations where other immunosuppressants are active as well.

These include the prevention and/or treatment of organ transplant rejection, the prevention and/or treatment of both rejection and the occurrence of graft-versus-host-disease after DM transplantation; the prevention and/or treatment of autoimmune diseases including diabetes mellitus, multiple sclerosis, glomerulonephritis, rheumatoid arthritis, proriasis systemic diseases such as vasculitis; scleroderma, polymyositis, autoimmune endocrine disorders (thyroiditis), ocular diseases (uveitis), inflammatory bowel diseases (Crohn's disease, colitis uclerosa), autoimmune liver diseases (autoimmune hepatitis, primary biliary cirrhosis) autoimmune pneumonitis and auto-immune carditis.

Whereas cyclosporine A and FK506 are only active in the anti-CD3+PMA test, the 8-substituted xanthine derivatives according to the invention were active, not only in the anti-CD3+PMA but also in the anti-CD28+PMA test. It has been shown that the latter is Ca-calmodulin resistant, and resistant to CsA and FK506. The anti-CD2a+PMA pathway has also been called the cosignal pathway and is important to induce energy and even tolerance in T cells. Moreover, representative compounds have been found to be active in a whole blood assay.

Under the term "organ" in the description is understood all organs or parts of organs (even several) in mammals, in particular humans, for example kidney, heart, skin, liver, muscle, cornea, bone, bone marrow, lung, pancreas, intestine or stomach.

After organ transplantation, rejection of the transplanted organ by the recipient occurs (host-versus-graft reaction). After bone marrow transplantation, also rejection of the host by the grafted cell may occur (graft-versus-host reaction). Rejection reactions mean all reactions of the recipient body or of the transplanted organ which in the end lead to cell or tissue death in the transplanted organ or adversely affect the functional ability and viability of the transplanted organ or adversely affect the functional ability and viability of the transplanted organ or the recipient. In particular, this means acute and chronic rejection reactions.

Auto-immune disorders include, inter alia, systemic lupus erythematosus, rheumatoid arthritis, psoriasis, pemphigus, atopic dermatitis, myositis, multiple sclerosis, nephrotic syndrome (in particular glomerulonephritis), ulcerative colitis or juvenile diabetes.

The invention further relates to the use of cyclosporin A or FK506 or Rapamycine and at least one 8-substituted xanthine according to the invention for the production of a pharmaceutical for inhibiting the replication of viruses such as picorna-, toga-, bunya-, orthomyxo-, paramyxo-, rhabdo-, retro-, arena-, hepatitis B-, hepatitis C-, hepatitis D-, adeno-, vaccinia-, papilloma-, herpes-, varicella-zoster-virus or human immunodeficiency virus (HIV); or for treating of cancer such as lung cancers, leukaemia, ovarian cancers, sarcoma, Kaposi's sarcoma, meningioma, colon cancers, lymp node tumors, glioblastoma multiforme, prostate cancers or skin carcinoses.

The invention further relates to the use of cyclosporin A or FK506 or rapamycin and at least one xanthine of the general formula for the production of a pharmaceutical for the treatment of human after organ transplantation or of (auto)immune disorders.

Hence, the advantage to associate xanthine with other immunosuppressants may be that, first, the therapeutic spectrum of action of the individual components is quantitatively and qualitatively broadened. Secondly that it allows, by means of a dose reduction without reduced efficacy but with increased safety, that the treatment of immune disorders which were hitherto no indication for immunosuppressive therapy as a result of side effects may be considered. At the same time, the therapy costs can be decreased to an appreciable extent.

The preferred compounds according to the invention are the xantine derivates bearing on the 8-position a substituted or unsubstituted phenyl.

The invention in particular relates to the use of a xanthine derivative of general formula (I):

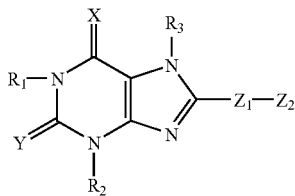

wherein:

$R_1$, $R_2$ and $R_3$ are independently hydrogen, saturated or unsaturated aliphatic chains which may be straight or branched having 1 to 6 carbon atoms;

X and Y are independently oxygen or sulfur;

$Z_1$ is selected from the group comprising a thienyl; furanyl; cyclopentyl, phenyl or a substituted by $Z_2$ or unsubstituted phenyl; wherein $Z_2$ is selected from the group comprising phenyl; sulfonic acid; unsubstituted or N-substituted sulfonamide with substituents such as alkyl, aminoalkyl where the amino group may be substituted itself with lower alkyl groups bearing 1 to 4 carbon atoms; nitro; halogen substituted or unsubstituted amino group; aliphatic chain with 1 to 3 carbon atoms; halogenated aliphatic chain with 1 to 3 carbon atoms; aliphatic chain containing ether functions, acids, esters, amides, substituted or unsubstituted amines having 1 to 3 carbon atoms, nitro, sulfonamides or a combination of these functional groups with a maximum length of the chain of 12 atoms, or a pharmaceutically acceptable salt thereof for the manufacture of a medicament for the treatment of auto-immuno disorders.

In a preferred embodiment $R_1$, $R_1$ and $R_3$ are independently hydrogen; saturated or unsaturated straight aliphatic chains having 1 to 3 carbon atoms; and $Z_1$ is a substituted or unsubstituted phenyl.

In another preferred embodiment the xanthine derivative is a compound selected from the group comprising:

1,7-diallyl-3-methyl-8-fenylxanthine (8);
1,3-dipropyl-8-[4(dimethylamino(ethyl(amino-(sulfonyl))))fenyl]xanthine (9);
1,3,7-trimethyl-8-(4-trifluoromethylfenyl)-xanthine (10);
1,3-dipropyl-8-[4(diethylamino(propyl(amino-(sulfonyl))))fenyl]xanthine (11);
1,3-dipropyl-2-thio-8-[4-((((N-2-aminoethyl)-amino)carbonyl)methyl)oxy)fenyl]xanthine (35);
1,3-dipropyl-8-[4-dimethylamino(propyl(amino-(sulfonyl))))fenyl]xanthine (40);
1,3-dimethyl-7-propyl-8-fenylxanthine (112);
1,7-diallyl-3-propyl-8-(p-bifenyl)xanthine (117);
1,3,7-tripropyl-8-(4-chlorofenyl)xanthine (118);
1,7-diallyl-3-propyl-8-(4-chlorofenyl)xanthine (119).

The invention further relates to a product containing a compound as mentioned above and at least a compound selected from the group comprising cyclosporine A, FK506, Rapamycin, Leflunomide, Mofetil.

The invention further relates to the use of a product as a combined preparation for simultaneous separate or sequential use in the treatment of auto-immuno disorders.

In a preferred embodiment the invention relates to a compound having the formula:

1-propynyl-3,7-dimethylxanthine (1);
1,7-dipropynyl-3-methylxanthine (2);
1-methyl-3,7-dipropynylxanthine (3);
1,3-dipropynyl-7-methylxanthine (4);
1,3,7-tripropynylxanthine (5);
1-(4-Carboxybutyl)-3,7-dimethylxanthine (22);
1-(3-carboxypropyl)-3,7-dimethylxanthine (23);
1-(3-ethoxycarbonyl)propyl-3,7-dimethylxanthine (24);
1,7-dimethyl-3-propynylxanthine (67);
1,7-dimethyl-3-((tertbutyl)methyl)xanthine (68);
1,3-dimethyl-7-allyl-8-[(4-trifluoromethyl)-fenyl]xanthine (82);
1,3-dimethyl-7-propyl-8-fenylxanthine (112);
1,3,7-tripropyl-8-fenylxanthine (113);
1,7-diallyl-3-propyl-8-fenylxanthine (114);
1,3,7-tripropyl-8-(p-bifenyl)xanthine (116);
1,7-diallyl-3-propyl-8-(p-bifenyl)xanthine (117);
1,3,7-tripropyl-α-(4-chlorofenyl)xanthine (118);
1,7-diallyl-3-propyl-8-(4-chlorofenyl)xanthine (119).

In another preferred embodiment the invention relates to a compound having the formula:

1-propynyl-3,7-dimethylxanthine (1);
1,7-dipropynyl-3-methylxanthine (2);
1-methyl-3,7-dipropynylxanthine (3);
1,3-dipropynyl-7-methylxanthine (4);
1,3,7-tripropynylxanthine (5).

In another preferred embodiment the invention relates to a compound having the formula:

1-(4-carboxybutyl)-3,7-dimethylxanthine (22);
1-(3-carboxypropyl)-3,7-dimethylxanthine (23);
1-(3-ethoxycarbonyl)propyl-3,7-dimethylxanthine (24).

In another preferred embodiment the invention relates to a compound having the formula:

1,3-dimethyl-7-allyl-8-[(4-trifluoromethyl)-fenyl]xanthine (82);
1,3-dimethyl-7-propyl-8-fenylxanthine (112);
1,3,7-tripropyl-8-fenylxanthine (113);
1,7-diallyl-3-propyl-8-fenylxanthine (114);
1,3,7-tripropyl-8-(p-bifenyl)xanthine (116).

In another preferred embodiment the invention relates to a compound having the formula:

1,7-diallyl-3-propyl-8-(p-bifenyl)xanthine (117);
1,3,7-tripropyl-8-(4-chlorofenyl)xanthine (118);
1,7-diallyl-3-propyl-8-(4-chlorofenyl)xanthine (119).

The invention further relates to the use of a compound as mentioned above for the manufacture of a medicament for the treatment of auto-immuno disorders.

TABLE I

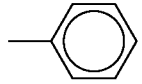

| Compound n° | R$_1$ | R$_2$ | R$_3$ | X | Y | Z$_1$ | Z$_2$ |
|---|---|---|---|---|---|---|---|
| 1 | CH$_2$C≡CH | CH$_3$ | CH$_3$ | O | O | H | — |
| 2 | CH$_2$C≡CH | CH$_3$ | CH$_2$C≡CH | O | O | H | — |
| 3 | CH$_3$ | CH$_2$C≡CH | CH$_2$C≡CH | O | O | H | — |
| 4 | CH$_2$C≡CH | CH$_2$C≡CH | CH$_3$ | O | O | H | — |
| 5 | CH$_2$C≡CH | CH$_2$C≡CH | CH$_2$C≡CH | O | O | H | — |
| 8 | CH$_3$—CH=CH$_2$ | CH$_3$ | CH$_2$—CH=CH$_2$ | O | O |  | — |
| 9 | CH$_2$CH$_2$CH$_3$ | CH$_2$CH$_2$CH$_3$ | H | O | O |  | —SO$_2$NHCH$_2$CH$_2$NMe$_2$ |
| 10 | CH$_3$ | CH$_3$ | CH$_3$ | O | O |  | CF$_3$ |
| 11 | CH$_2$CH$_2$CH$_3$ | CH$_2$CH$_2$CH$_3$ | H | O | O |  | —SO$_2$NH(CH$_2$)$_3$NEt$_2$ |
| 12 | CH$_2$—CH=CH$_3$ | CH$_3$ | CH$_3$ | O | O |  | CF$_3$ |
| 13 | CH$_2$CH$_2$CH$_3$ | CH$_2$CH$_2$CH$_3$ | H | O | O |  | —OCH$_2$CONH(CH$_2$)$_2$NEt$_2$ |
| 14 | CH$_2$CH$_2$CH$_3$ | CH$_2$CH$_2$CH$_3$ | CH$_2$CH=CH$_2$ | O | O | 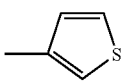 | CF$_3$ |
| 15 | CH$_2$CH$_2$CH$_3$ | CH$_2$CH$_2$CH$_3$ | H | O | O |  | — |
| 16 | CH$_2$CH$_2$CH$_3$ | CH$_2$CH$_2$CH$_3$ | H | O | S | 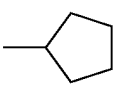 | SO$_2$NH$_2$ |
| 17 | CH$_3$ | CH$_3$ | H | S | O | 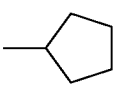 | — |
| 18/ | CH$_3$ | CH$_3$ | H | S | S | 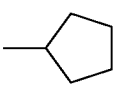 | — |
| 19 | CH$_3$ | CH$_3$ | CH$_3$ | O | O | 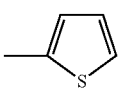 | — |

TABLE I-continued

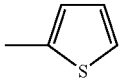

| Compound n° | R₁ | R₂ | R₃ | X | Y | Z₁ | Z₂ |
|---|---|---|---|---|---|---|---|
| 20 | $CH_3$ | $CH_3$ | $CH_3$ | O | S | 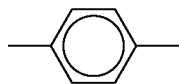 | — |
| 21 | $CH_2CH=CH_3$ | $CH_3$ | $CH_3$ | O | O |  | $SO_3Na$ |
| 22 | —$(CH_2)_3COOH$ | $CH_3$ | $CH_3$ | O | O | H | — |
| 23 | —$(CH_2)_3COOH$ | $CH_3$ | $CH_3$ | O | O | H | — |
| 24 | —$(CH_2)_3COOEt$ | $CH_3$ | $CH_3$ | O | O | H | — |
| 25 | —$(CH_2)_4CHOH—CH_3$ | $CH_3$ | $CH_3$ | O | O | H | — |
| 26 | —$(CH_2)_4CHOH—CH_3$ | $CH_3$ | $CH_2CH_2CH_3$ | O | O | H | — |
| 28 | —$CH_2CH_2CH_3$ | $CH_2CH_2CH_3$ | H | O | S |  | —$OCH_2COOH$ |
| 29 | —$CH_2CH_2CH_3$ | $CH_2CH_2CH_3$ | H | O | S |  | —$OCH_2COOEt$ |
| 30 | $CH_2CH_2CH_3$ | $CH_2CH_2CH_3$ | H | O | O |  | $OCH_2COOMe$ |
| 31 | $CH_2CH_2CH_3$ | $CH_2CH_2CH_3$ | H | O | O | 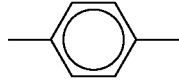 | $OCH_2CONH(CH_2)_2NHCOCH_3$ |
| 32 | $CH_2CH_2CH_3$ | $CH_2CH_2CH_3$ | H | O | O | 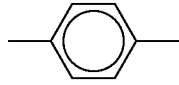 | $OCH_2CONH(CH_3)_2NHSO_3H$ |
| 33 | $CH_2CH_2CH_3$ | $CH_2CH_2CH_3$ | H | O | O | 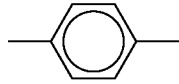 | $OCH_2CONH(CH_2)_2—NH_2$ |
| 34 | $CH_2CH_2CH_3$ | $CH_2CH_2CH_3$ | H | O | O | 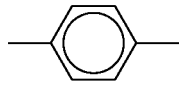 | $OCH_2CONH(CH_2)_2NMe_2$ |
| 35 | $CH_2CH_2CH_3$ | $CH_2CH_2CH_3$ | H | O | S | 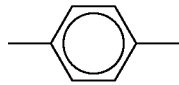 | $OCH_2CONH(CH_2)_2NH_3$ |
| 36 | $CH_2CH_2CH_3$ | $CH_2CH_2CH_3$ | H | O | O | 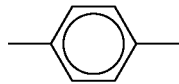 | —$SO_2NH_2$ |
| 37 | H | $CH_3$ | $CH_3$ | O | O |  | $SO_2NH_2$ |

TABLE I-continued
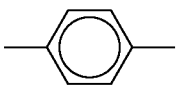
| Compound n° | R₁ | R₂ | R₃ | X | Y | Z₁ | Z₂ |
|---|---|---|---|---|---|---|---|
| 38 | H | $CH_3$ | $CH_3$ | O | O | 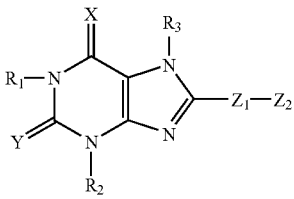 | $SO_3H$ |
| 39 | $CH_3$ | $CH_3$ | H | O | O | 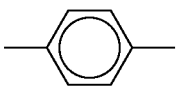 | $SO_2NH(CH_2)_2NH_2$ |
| 40 | $CH_2CH_2CH_3$ | $CH_2CH_2CH_3$ | H | O | O | 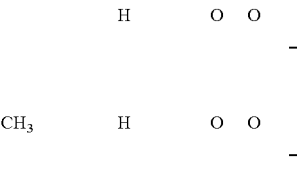 | $SO_2NH(CH_2)_2NMe_2$ |
| 41 | $CH_3$ | $CH_3$ | H | O | O |  | $SO_2NH(CH_2)_2NMe_2$ |
| 42 | $CH_3$ | $CH_3$ | H | O | O | 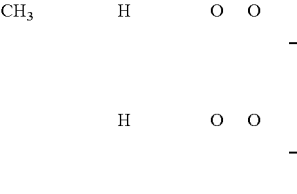 | $SO_2NH(CH_2)_2NMe_2$ |
| 43 | $CH_3$ | $CH_3$ | H | O | O |  | $SO_2NH(CH_2)_2NEt_2$ |
| 44 | $CH_3$ | $CH_3$ | H | O | S | 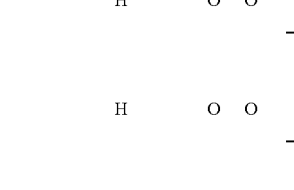 | — |
| 45 | $CH_3$ | $CH_3$ | H | S | O |  | — |
| 46 | $CH_2CH_3$ | $CH_2CH_3$ | H | S | O | 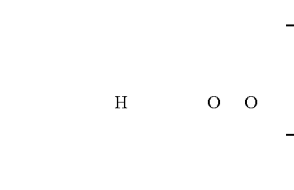 | — |
| 47 | H | $CH_3$ | $CH_3$ | O | O | 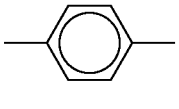 | — |
| 48 | $CH_2CH_2CH_3$ | $CH_2CH_2CH_3$ | H | O | O | 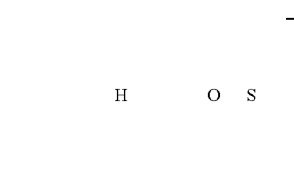 | $CF_3$ |
| 50 | $CH_2CH=CH_2$ | $CH_3$ | $CH_3$ | O | O | 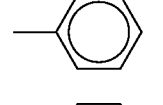 | — |
| 51 | $CH_3$ | $CH_3$ | H | O | O | 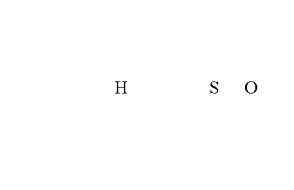 | $CF_3$ |

TABLE I-continued

| Compound n° | R₁ | R₂ | R₃ | X | Y | Z₁ | Z₂ |
|---|---|---|---|---|---|---|---|
| 52 | CH₃ | CH₃ | H | O | O | *p*-phenylene | NO₂ |
| 53 | CH₂CH₂CH₃ | CH₂CH₂CH₃ | H | O | O | *p*-phenylene | NO₂ |
| 54 | CH₂CH₂CH₃ | CH₂CH₂CH₃ | H | O | O | *p*-phenylene | NH₂ |
| 55 | CH₃ | CH₃ | H | O | O | 2-thienyl | — |
| 56 | CH₂CH₂CH₃ | CH₂CH₂CH₃ | H | O | O | 2-thienyl | — |
| 57 | CH₃ | CH₃ | H | O | S | 2-thienyl | — |
| 58 | CH₃ | CH₃ | H | O | O | 2-furyl | — |
| 59 | CH₂CH₂CH₃ | CH₂CH₂CH₃ | H | O | O | 2-furyl | — |
| 60 | CH₃ | CH₃ | H | O | S | 2-furyl | — |
| 61 | CH₂CH₂CH₃ | CH₂CH₂CH₃ | H | O | S | 2-furyl | — |
| 62 | CH₃ | CH₃ | H | O | O | cyclopentyl | — |
| 63 | CH₂CH₂CH₃ | CH₂CH₂CH₃ | H | O | O | cyclopentyl | — |
| 64 | CH₃ | CH₃ | H | O | S | cyclopentyl | — |
| 65 | CH₂CH₂CH₃ | CH₂CH₂CH₃ | H | O | S | cyclopentyl | — |

TABLE I-continued

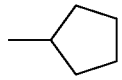

| Compound n° | $R_1$ | $R_2$ | $R_3$ | X | Y | $Z_1$ | $Z_2$ |
|---|---|---|---|---|---|---|---|
| 66 | $CH_3$ | $CH_3$ | $CH_3$ | O | S | 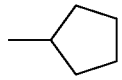 | — |
| 67 | $CH_3$ | $CH_2C{=}CH$ | $CH_3$ | O | O | H | — |
| 68 | $CH_3$ | $CH_2C(CH_3)_2$ | $CH_3$ | O | O | H | — |
| 69 | $CH_3$ | $CH_3{-}C(CH_3)_2$ | H | O | O | H | — |
| 70 | H | $CH_2C(CH_3)_2$ | $CH_3$ | O | O | H | — |
| 71 | $CH_3$ | $-CH(CH_3)_2$ | H | O | O | H | — |
| 78 | $CH_3$ | $CH_3$ | H | O | O | 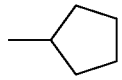 | — |
| 79 | $CH_3$ | $CH_3$ | $CH_3$ | O | O | 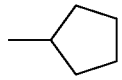 | — |
| 80 | $CH_2CH_2CH_3$ | $CH_2CH_2CH_3$ | H | O | O | 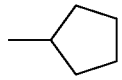 | — |
| 81 | $CH_2CH_2CH_3$ | $CH_2CH_2CH_3$ | H | O | S | 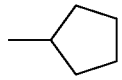 | |
| 82 | $CH_3$ | $CH_3$ | $CH_2CH{=}CH_2$ | O | O | 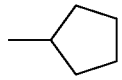 | $CF_3$ |
| 83 | H | $CH_3$ | $CH_3$ | O | O | 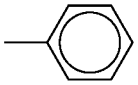 | $CF_3$ |
| 112 | $CH_3$ | $CH_3$ | $CH_2CH_2CH_3$ | O | O | 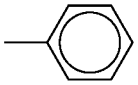 | — |
| 113 | $CH_2CH_2CH_3$ | $CH_2CH_2CH_3$ | $CH_2CH_2CH_3$ | O | O | 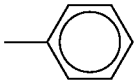 | — |
| 114 | $CH_2{-}CH{=}CH_2$ | $-CH_2CH_2CH_3$ | $CH_3{-}CH{=}CH_2$ | O | O | 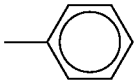 | — |
| 115 | $CH_3$ | $CH_3$ | H | O | O | 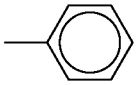 | 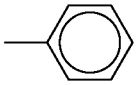 |
| 116 | $CH_2CH_2CH_3$ | $CH_2CH_2CH_3$ | $CH_2CH_2CH_3$ | O | O | 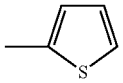 | 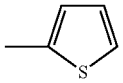 |

TABLE I-continued

| Compound n° | R₁ | R₂ | R₃ | X | Y | Z₁ | Z₂ |
|---|---|---|---|---|---|---|---|
| 117 | CH₂—CH=CH₂ | CH₂CH₂CH₃ | CH₂—CH=CH₂ | O | O | —C₆H₄— | —C₆H₅ |
| 118 | CH₂CH₂CH₃ | CH₂CH₂CH₃ | CH₂CH₂CH₃ | O | O | —C₆H₄— | Cl |
| 119 | CH₂—CH=CH₂ | CH₂CH₂CH₃ | CH₂—CH=CH₂ | O | O | —C₆H₄— | Cl |
| 125 | CH₃ | CH₃ | H | O | O | —C₆H₄— | —SO₂NH₂ |

TABLE II

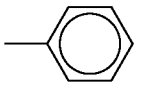

| | R₁ | R₂ | R₃ | Z₁ | Z₂ | Mp |
|---|---|---|---|---|---|---|
| 1a | H | CH₃ | CH₃ | H | — | |
| 1 | HC≡C—CH₂ | CH₃ | CH₃ | H | — | 204° |
| 2a | H | CH₃ | H | H | — | |
| 2 | HC≡C—CH₂ | CH₃ | HC≡C—CH₂ | H | — | 177° |
| 3a | CH₃ | H | H | H | — | |
| 3 | CH₃ | HC≡C—CH₂ | HC≡C—CH₂ | H | — | 174° |
| 4a | H | H | CH₃ | H | — | |
| 4 | HC≡C—CH₂ | HC≡C—CH₂ | CH₃ | H | — | 172° |
| 5a | H | H | H | H | — | |
| 5 | HC≡C—CH₂ | HC≡C—CH₂ | HC≡C—CH₂ | H | — | 155° |
| 22 | HOOC(CH₂)₄ | CH₃ | CH₃ | H | — | 195° |
| 23 | HOOC(CH₂)₃ | CH₃ | CH₃ | H | — | 208-210° |
| 24 | EtOOC(CH₂)₃ | CH₃ | CH₃ | H | — | 86-88° |
| 67a | CH₃ | H | CH₃ | H | — | |
| 67 | CH₃ | HC≡C—CH₂ | CH₃ | H | — | |
| 68a | H | CH₂C(CH₃)₃ | H | H | — | |
| 68 | CH₃ | CH₂C(CH₃)₃ | CH₃ | H | — | 158° |
| 82a | CH₃ | CH₃ | H | —C₆H₄— | p-CF₃ | |
| 82 | CH₃ | CH₃ | CH₂=CHCH₂ | —C₄H₄— | p-CF₃ | 116-118° |
| 112a | CH₃ | CH₃ | H | —C₆H₅ | — | |
| 112 | CH₃ | CH₃ | CH₃CH₂CH₂ | —C₆H₅ | — | 141° |
| 113a | H | CH₃CH₂CH₂ | H | —C₆H₅ | — | |
| 113 | CH₃CH₂CH₂ | CH₃CH₂CH₂ | CH₃CH₂CH₂ | —C₆H₅ | — | 123-125° |
| 114a | H | CH₃CH₂CH₂ | H | —C₆H₅ | — | |
| 114 | CH₂=CHCH₂ | CH₃CH₂CH₂ | CH₂=CHCH₂ | —C₆H₅ | — | 113-114° |
| 116a | H | CH₃CH₂CH₂ | H | —C₆H₄ | p-C₆H₅ | |
| 116 | CH₃CH₂CH₂ | CH₃CH₂CH₂ | CH₃CH₂CH₂ | —C₆H₄ | p-C₆H₅ | 116° |
| 117a | H | CH₃CH₂CH₂ | H | —C₆H₄ | p-C₆H₅ | |
| 117 | CH₂=CHCH₂ | CH₃CH₂CH₄ | CH₂=CHCH₂ | —C₆H₄ | p-C₆H₅ | 104-106° |
| 118a | H | CH₃CH₂CH₂ | H | —C₆H₄ | p-Cl | |

TABLE II-continued

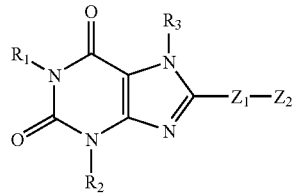

| | R₁ | R₂ | R₃ | Z₁ | Z₂ | Mp |
|---|---|---|---|---|---|---|
| 118 | CH₃CH₂CH₂ | CH₃CH₂CH₂ | CH₃CH₂CH₂ | —C₆H₄ | p-Cl | 71-74° |
| 119a | H | CH₃CH₂CH₂ | H | —C₆H₄ | p-Cl | |
| 119 | CH₂=CHCH₂ | CH₃CH₂CH₂ | CH₂=CHCH₂ | —C₆H₄ | p-Cl | 89-91° |

TABLE III

| | R₁ | R₂ | R₃ | X | Z₁ | Z₂ | Mp |
|---|---|---|---|---|---|---|---|
| 16 | CH₃CH₂CH₂ | CH₃CH₂CH₂ | H | S | —C₆H₄ | p-SO₂NH₂ | >300° |
| 25 | CH₃CHOH(CH₂)₄ | CH₃ | CH₃ | | | | 118–120° |
| 26 | CH₃CHOH(CH₂)₄ | CH₃ | CH₃CH₂CH₂ | | | | 72–74° |
| 52 | CH₃ | CH₃ | H | O | —C₄H₄ | p-NO₂ | 275° |
| 53 | CH₃CH₂CH₂ | CH₃CH₂CH₂ | H | O | —C₆H₄ | p-NO₂ | >270° |
| 54 | CH₃CH₂CH₂ | CH₃CH₂CH₂ | H | O | —C₆H₄ | p-NO₂ | >300° |
| 69 | CH₃ | CH₂C(CH₂)₃ | H | O | H | — | 234° |
| 70 | H | CH₂C(CH₂)₃ | CH₃ | O | H | — | 248° |
| 71 | CH₃ | CH(CH₃)₂ | H | O | H | — | 230° |
| 115 | CH₃ | CH₃ | H | O | —C₆H₄— | p-C₄H₅ | >300° |

TABLE IV

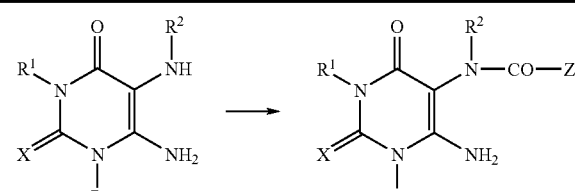

| | R | R¹ | R² | X | | R | R¹ | R² | X | Z | M.p. |
|---|---|---|---|---|---|---|---|---|---|---|---|
| 16b | n-Pr | n-Pr | H | S | 16a | n-Pr | n-Pr | H | S | p-C₆H₄—SO₃NH₃ | 268-270° |
| 52b | Me | Me | H | O | 52a | Me | Me | H | O | p-C₆H₄—NO₂ | |
| 53b | n-Pr | n-Pr | H | O | 53a | n-Pr | n-Pr | H | O | p-C₆H₄—NO₂ | >250° dec |
| 69b | CH₂CMe₂ | Me | H | O | 54a | n-Pr | n-Pr | H | O | p-C₆H₄—NH₂ | |
| 71b | CHMe₂ | Me | H | O | 69a | CH₂CMe₃ | Me | H | O | H | 235-237° |
| 70b | CH₂CMe₃ | H | Me | O | 71a | CHMe₂ | CH₃ | H | O | H | |
| 116b | n-Pr | H | H | O | 70a | CH₂CMe₃ | H | CH₃ | O | H | 267-270° |
| | | | | | 116b | n-Pr | H | H | O | 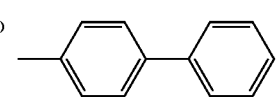 | 288-290° |
| | | | | | 115a | Me | Me | H | O | 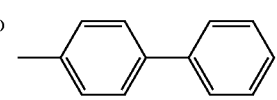 | 180° |
| | | | | | 118b | n-Pr | H | H | O |  | 269-272° |

TABLE V

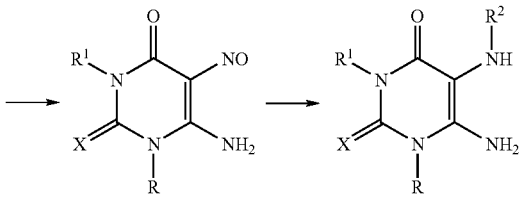

| R | R¹ | X | | R | R¹ | R² | X | M.p. |
|---|---|---|---|---|---|---|---|---|
| 70c | $CH_2CMe_3$ | H | O | 70b | $CH_2CMe_3$ | H | Me | O | >237° dec |
| 69c | $CH_2CMe_3$ | Me | O | 69b | $CH_2CMe_3$ | Me | H | O | 108-110° |
| 16c | n-Pr | n-Pr | S | 16b | n-Pr | n-Pr | H | S | 110-113° |
| 52c | Me | Me | O | 52b | Me | Me | H | O | |
| 53c | n-Pr | n-Pr | O | 53b | n-Pr | n-Pr | H | O | |
| 71c | $CHMe_2$ | Me | O | 71b | $CHMe_3$ | Me | H | O | |
| 116d | n-Pr | H | O | 116c | n-Pr | H | H | O | |

TABLE VI

| | IC50 in μM | | |
|---|---|---|---|
| | Xanthine derivatives | | |
| Nr | MLR | aCD3 | aCD28 |
| 1 | >200 | 150 | >200 |
| 2 | >200 | >200 | 100 |
| 3 | 150 | 150 | 100 |
| 4 | >200 | 90 | >200 |
| 5 | >200 | 50 | >200 |
| 8 | 30 | 35 | 80 |
| 9 | 25 | 40 | 50 |
| 10 | 50 | 20 | 30 |
| 11 | 25 | 40 | 55 |
| 12 | 30 | 90 | 80 |
| 13 | ND | 35 | 40 |
| 14 | 15 | 40 | 35 |
| 15 | ND | >200 | 170 |
| 16 | ND | 25 | 20 |
| 17 | 80 | 30 | 40 |
| 18 | 120 | 75 | 40 |
| 19 | ND | 50 | 80 |
| 20 | ND | 170 | 50 |
| 21 | ND | 180 | 80 |
| 22 | >200 | >200 | >200 |
| 23 | >200 | >200 | >200 |
| 24 | >200 | 170 | 150 |
| 25 | >200 | 140 | 160 |
| 26 | 100 | 100 | 100 |
| 28 | 120 | 150 | 75 |
| 29 | >200 | 150 | 130 |
| 30 | >200 | 140 | 100 |
| 31 | 200 | 120 | 80 |
| 32 | 70 | 90 | 110 |
| 33 | 160 | 45 | 35 |
| 34 | 105 | 45 | 60 |
| 35 | 50 | 50 | 70 |
| 36 | >200 | 45 | 40 |
| 37 | >200 | 150 | 150 |
| 38 | >200 | 120 | 120 |
| 39 | 100 | 120 | 140 |
| 40 | 25 | 60 | 70 |
| 41 | 120 | 80 | 90 |
| 42 | 170 | 130 | 130 |
| 43 | 115 | 120 | 90 |
| 44 | 120 | 170 | 120 |
| 45 | 165 | 25 | 25 |
| 46 | >200 | 25 | 20 |
| 47 | 200 | 140 | 140 |
| 48 | 180 | 160 | 150 |
| 49 | ND | ND | ND |
| 50 | 180 | 200 | 120 |
| 51 | 200 | 200 | 200 |
| 52 | 80 | 180 | 90 |
| 53 | 110 | 160 | 110 |
| 54 | 120 | 130 | 130 |
| 55 | >200 | 200 | 120 |
| 56 | >200 | 170 | 100 |
| 57 | >200 | >200 | 180 |
| 58 | >200 | 160 | 170 |
| 59 | 15 | 155 | 135 |
| 60 | >200 | 200 | 190 |
| 61 | 100 | 170 | 110 |
| 62 | >200 | >200 | 190 |
| 63 | >200 | 135 | 100 |
| 64 | >200 | >200 | >200 |
| 65 | >200 | 135 | 75 |
| 66 | >200 | 170 | 170 |
| 67 | >200 | >200 | 200 |
| 68 | 75 | 130 | 120 |
| 69 | 120 | 110 | 45 |
| 70 | >200 | 180 | 140 |
| 71 | 160 | | |
| 77 | 130 | | |
| 78 | >200 | >200 | >200 |
| 79 | 75 | 100 | 130 |
| 80 | 160 | 120 | 65 |
| 81 | >200 | 180 | 110 |
| 82 | 25 | 80 | 80 |
| 83 | >200 | >200 | 150 |
| 112 | 20 | 45 | 40 |
| 113 | 20 | 110 | 90 |
| 114 | 15 | 85 | 70 |
| 115 | 110 | >200 | 160 |
| 116 | 160 | 45 | 40 |
| 117 | 15 | 30 | 30 |
| 118 | 15 | 15 | 20 |
| 119 | 15 | 50 | 30 |
| 125 | 160 | 150 | 90 |
| 132 | >200 | >200 | >200 |

| | IC50 | | |
|---|---|---|---|
| | Immunosuppressant | | |
| LS. | MLR | aCD3 | aCD28 |
| CyA | 20 nM | 50 nM | N.S. |
| FK506 | 1 nM | 1 nM | N.S. |
| Rapamycin | 1 nM | 1 nM | 1 nM |
| Leflunomide | 25 μM | 15 μM | 20 μM |
| Moferil | <0.5 μM | 50 nM | 50 nM |

N.S. = not suppressive even not in the highest concentration

What is claimed is:

1. An immunosuppressive composition in unit dosage form for immunosuppression incident to organ transplantation and xenogenic events comprising:
   a) a first immunosuppressive compound having general Formula (I), as follows:

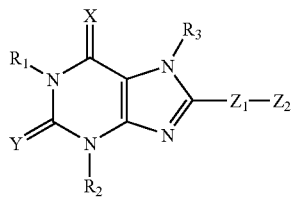

wherein $R_1$, $R_2$ and $R_3$ are independently hydrogen, saturated or unsaturated, straight or branched $C_{1-6}$ aliphatic chains,
   X and Y are independently oxygen or sulfur,
   $Z_1$ is selected from the group consisting of an unsubstituted thienyl group and an unsubstituted furanyl group, and
   $Z_2$ is selected from the group consisting of a phenyl group; a sulfonic acid group; an unsubstituted sulfonamide group; a substituted sulfonamide group that is substituted with one of an alkyl group, an unsubstituted aminoalkyl group and a $C_{1-4}$ alkyl-substituted aminoalkyl group; an amino group; a halogen-substituted amino group; a $C_{1-3}$ aliphatic group; a halogen-substituted $C_{1-3}$ aliphatic group and a $C_{1-12}$ aliphatic group that is substituted with one or more functional groups selected from the group consisting of an ester group, an amide group, an unsubstituted amine group, a $C_{1-3}$ alkyl-substituted amine group and a sulfonamide group, or a pharmaceutically acceptable salt thereof in an amount effective to cause immunosuppression in a patient; and
   b) a pharmaceutically acceptable excipient.

2. The immunosuppressive composition of claim 1 in which the first immunosuppressive compound is a compound having the general formula (I):

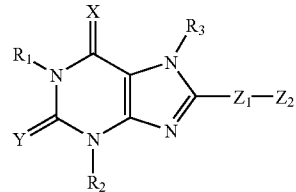

wherein $R_1$, $R_2$ and $R_3$ are independently hydrogen, a $C_{1-4}$ alkane, alkene or alkyne, a carboxyl-substituted $C_{1-4}$ alkane or alkene and an ethoxycarbonyl-substituted $C_{1-4}$ alkane or alkene, wherein; no more than one of $R_1$, $R_2$ and $R_3$ are hydrogen; X and Y are independently oxygen or sulfur, $Z_1$ is an unsubstituted thienyl group and $Z_2$ is selected from the group consisting of hydrogen, chloride, phenyl, and trifluoromethyl when $R_1$, $R_2$ and $R_3$ are all $C_{1-4}$ alkane or alkene.

3. The immunosuppressive composition of claim 1, the composition further comprising a second immunosuppressive compound.

4. The immunosuppressive composition of claim 3 in which the second immunosuppressive compound is selected from the group consisting of cyclosporin A, tacrolimus, rapamycin, leflunomide and mofetil.

* * * * *